US006955646B2

(12) United States Patent
Christ et al.

(10) Patent No.: US 6,955,646 B2
(45) Date of Patent: Oct. 18, 2005

(54) METHOD AND MEDICAL SYSTEM FOR THE POSTDISCHARGE SURVEILLANCE OF A PATIENT

(75) Inventors: Tilo Christ, Erlangen (DE); Volker Schmidt, Erlangen (DE); Hans Schüll, Weisendorf (DE); Werner Striebel, Schwarzenbruck (DE)

(73) Assignee: Siemens Aktiengesellschaft, Munich (DE)

( * ) Notice: Subject to any disclaimer, the term of this patent is extended or adjusted under 35 U.S.C. 154(b) by 177 days.

(21) Appl. No.: 10/053,713

(22) Filed: Jan. 24, 2002

(65) Prior Publication Data

US 2002/0115913 A1 Aug. 22, 2002

(30) Foreign Application Priority Data

Jan. 25, 2001 (DE) .......................................... 101 03 325

(51) Int. Cl.⁷ ................................................ A61B 5/00
(52) U.S. Cl. ........................ 600/300; 128/920; 128/904; 705/4
(58) Field of Search ................................ 600/300–301, 600/369; 128/903–905, 920–925, 898; 705/1–4; 340/573.1–576; 434/236–238, 262

(56) References Cited

U.S. PATENT DOCUMENTS

| | | | |
|---|---|---|---|
| 5,339,821 A | 8/1994 | Fujimoto | |
| 5,416,695 A | 5/1995 | Stutman et al. | |
| 5,544,661 A | 8/1996 | Davis et al. | |
| 5,553,609 A | 9/1996 | Chen et al. | |
| 5,967,975 A | * 10/1999 | Ridgeway | 600/300 |
| 6,206,829 B1 | * 3/2001 | Iliff | 600/300 |
| 6,409,662 B1 | * 6/2002 | Lloyd et al. | 600/300 |
| 6,443,734 B1 | * 9/2002 | Rappaport | 434/236 |
| 6,454,705 B1 | * 9/2002 | Cosentino et al. | 600/300 |

FOREIGN PATENT DOCUMENTS

| | | |
|---|---|---|
| DE | 200 10 374 U1 | 8/2000 |
| EP | 1 034 734 A1 | 9/2000 |
| EP | 1 101 437 A1 | 5/2001 |
| FR | 2 717 332 | 9/1995 |
| FR | 2 750 236 | 12/1997 |
| WO | WO 93/01574 | 1/1993 |
| WO | 98/24212 | 6/1998 |

OTHER PUBLICATIONS

Medical Centre Daniël den Hoed ses laptops for tele–home–monitoring of cancer patients published on Dec. 8, 2000.*

* cited by examiner

Primary Examiner—Max F. Hindenburg
Assistant Examiner—Michael Astorino
(74) Attorney, Agent, or Firm—Young & Thompson

(57) ABSTRACT

A method and medical system for the postdischarge surveillance of a patient (1) for detecting a case of pneumonia, secondary bleeding, a wound healing problem, a pulmonary complication, a urinary tract infection or a thrombosis of the patient (1), having a data bank (13), which is arranged at a location other than the location (2) at which the patient (1) is based during the surveillance and stores data relevant for the postdischarge surveillance of the patient (1) recorded during the postdischarge surveillance.

10 Claims, 2 Drawing Sheets

Questionnaire for the patient 1

General condition

| | |
|---|---|
| Physical capabilities | ☐ good   ☐ moderate   ☐ poor |
| Appetite | ☐ good   ☐ moderate   ☐ poor |
| Temperature | _____ °C |
| Bowel movement | ☐ unremarkable      ☐ remarkable |
| Pulse | _____ |
| Blood pressure | _____ |
| Blood sugar | _____ |

Lung complications

| | |
|---|---|
| Coughing | ☐ good   ☐ moderate   ☐ poor |
| Expectoration | ☐ good   ☐ moderate   ☐ poor |
| Respiration rate | _____ Hz |

Date: _____

FIG 2

METHOD AND MEDICAL SYSTEM FOR THE POSTDISCHARGE SURVEILLANCE OF A PATIENT

The invention relates to a method and medical system for the postdischarge surveillance of a patient.

BACKGROUND OF THE INVENTION

After a patient has undergone an operation, typical postoperative complications can occur, including cases of pneumonia, inflammation of the lungs and bronchitis, urinary tract infections, secondary bleeding, leg and pelvic venous thromboses, hypoglycemia and wound healing problems. With a current trend to shorten the time a patient stays in hospital, patients are also discharged from hospital earlier after an operation. As a result, there is the risk of possibly occurring postoperative complications being detected too late.

SUMMARY OF THE INVENTION

The invention is therefore based on the object of providing a method and designing a medical system in such a way that they can be used to create the preconditions that, in particular, postoperative complications are detected reliably and at an early stage, although the patient has been discharged early from hospital.

According to the invention, this object is achieved by a method for the postdischarge surveillance of a patient for detecting a case of pneumonia, secondary bleeding, a wound healing problem, a pulmonary complication, a urinary tract infection or a thrombosis of the patient, for the implementation of which a data bank is provided, arranged at a location other than the location at which the patient is based during the surveillance, having the following method steps:

a) recording relevant data on the patient for the postdischarge surveillance of the latter and b) transmitting the relevant data to the data bank.

According to the invention, the patient is consequently kept under postdischarge surveillance to detect a case of pneumonia, secondary bleeding, a wound healing problem, a pulmonary complication, a urinary tract infection or a thrombosis, that is typical postoperative complications, at an early stage. The postdischarge surveillance of a patient, that is as an outpatient, has the effect, in particular, of saving costs of providing care. The patient looks after himself, for example at his home, or is cared for by a relative, for example, or an outpatient care provider. To ensure proper postdischarge surveillance of the patient, the patient or another person records data on the patient relevant for the detection of typical complications. For the detection of secondary bleeding, these data include the time at which secondary bleeding is discovered, signs of centralization, blood pressure, heart rate or visible bleeding. For a wound healing problem, the relevant data include pain, overheating, reddening, restriction of mobility and hypoglycemia of the patient. Data relevant for a pulmonary complication comprise expectoration, coughing or fever. For a urinary tract infection, the relevant data comprise pain when passing water, nycturia or pollakiuria and, for a thrombosis, the relevant data comprise pain in the calf or leg, type of operation, circumferences of the legs, comparing each side and how they vary, and variation in leg temperature. The circumferences of the legs can be measured, for example, with a tape measure, overheating can be measured with an infrared camera or a skin thermometer and fever can be measured with a fever thermometer. What is more, during surveillance, the patient can be provided with a blood-sugar measuring instrument, urine sticks, a blood-pressure measuring instrument or a digital camera for monitoring a wound. After recording the relevant data, they are transmitted to the central data bank, which is arranged for example at the hospital in which the patient was treated. A doctor treating the patient consequently has easy access to the relevant data. This provides the preconditions for detecting complications at an early stage and reliably, although the patient is not being treated as an inpatient.

According to a preferred variant of the invention, the data bank is operated by a service provider. Such a service provider can maintain the data bank or provide further services in a particularly favorable way. In particular, if, according to one variant of the invention, a call center is assigned to the service provider, questions from the patient or the doctor can be directed to the call center. Consequently, patient care can be made more effective and, if there are questions, further help can be provided in a quick, friendly and reliable way.

In the case of a further advantageous embodiment of the invention, the relevant data are recorded by means of a questionnaire. This questionnaire may, for example, be in paper form and among the items given to the patient upon discharge from the hospital, or can be called up on a world wide web (WWW) home page assigned to the patient and maintained, for example, by the service provider. The questionnaire may also serve as a checklist, in order that the patient or other person ascertains all the relevant data.

According to one embodiment of the invention, relevant data also comprise a description of the general condition of the patient. The general condition of the patient can be checked, for example, by ascertaining the physical capabilities, for example when climbing stairs. The appetite, temperature, bowel movement, pulse, blood pressure or blood sugar of the patient likewise allow conclusions to be drawn concerning the general condition of the patient. Consequently, the relevant data may comprise, in particular, a description of the general condition in combination with data for detecting a typical complication. A typical complication after general anesthesia with intubation is, for example, an inflammation of the lungs. Consequently, the relevant data after general anesthesia with intubation comprise, in particular, data for detecting a pulmonary complication and information on the general condition of the patient.

According to a further embodiment of the invention, the relevant data are transmitted at least indirectly to the data bank by a telephone, a computer which can be connected to the Internet or a fax machine. In particular in the case of transmission by telephone, the patient does not have to be provided with a complicated and possibly costly transmission device during the postdischarge surveillance, since generally every household is equipped with a telephone. A suitably configured measuring instrument can also be connected to the computer. Consequently, the values ascertained with the measuring instrument can be transmitted to the data bank by the computer and reading errors are avoided.

If, according to a preferred embodiment of the invention, the data bank can be interrogated via the Internet, the doctor treating the patient, for example, has easy access to the relevant data and can consequently discover possibly arising complications of the patient at an early stage and reliably and, if necessary, initiate remedial measures.

In the case of a further variant of the invention, it is provided that the data bank automatically informs the patient and/or at least one other person if the relevant data are not received. The other person is, for example, the doctor treating the patient. This provides the precondition that the patient can be reminded of the importance of the surveillance, in particular if he inadvertently forgot to ascertain or transmit the relevant data, or that the doctor is quickly and reliably informed if there is an interruption in the surveillance.

According to a further advantageous embodiment of the invention, the relevant data are evaluated, in particular automatically, by an evaluation device assigned to the data bank. The evaluation device may have, in particular, an expert system which interprets the relevant data context-dependently and, for example in the case of unclear situations, asks the patient follow-up questions. What is meant, inter alia, by context-dependent interpretation is that the relevant data are compared with corresponding data assigned to a patient who did not have any postoperative complications. An advantage of an automated evaluation is the saving on personnel. What is more, it is consequently ensured that an evaluation of the relevant data is not inadvertently overlooked.

In the case of a particularly advantageous form of the invention, it is provided that the data bank automatically alerts the patient and/or at least one other person if the evaluated relevant data are critical. For example, the average course of painkiller consumption after a specific operation on a number of patients who did not have any complications could be ascertained and stored in the data bank. The average course of painkiller consumption can then serve as an alarm limit. The other person may, for example, be the doctor treating the patient, who is able, for example, on the basis of the alarm to check the data and, if necessary, initiate emergency measures for the patient quickly and reliably.

The object is also achieved by a medical system for the postdischarge surveillance of a patient for detecting a case of pneumonia, secondary bleeding, a wound healing problem, a pulmonary complication, a urinary tract infection or a thrombosis of the patient, having a data bank which is arranged at a location other than the location at which the patient is based during the surveillance and stores data relevant for the postdischarge surveillance of the patient recorded during the postdischarge surveillance, an evaluation device assigned to the data bank for the evaluation of the relevant data and an alarm device for generating an alarm signal if the evaluated relevant data are critical. The medical system is consequently characterized in that, in particular, typical postoperative complications of a patient can be detected at an early stage, although the patient was, in particular, discharged at an early stage from the hospital. During the postdischarge surveillance, the patient or another person, such as for example a relative or a caregiver, records data relevant for the detection of complications and transmits them to a central data bank. The data bank may, for example, be arranged at the hospital in which the patient was treated. Consequently, on the one hand the patient does not have to be treated as an inpatient, thereby saving costs, and on the other hand the doctor treating the patient has the possibility at any time of viewing the relevant data and accordingly detecting complications at an early stage and, if necessary, initiating remedial measures for the patient.

In the case of an advantageous refinement of the invention, the data bank is conFIG.d in such a way that it automatically informs the patient and/or at least one other person if the relevant data are not received.

BRIEF DESCRIPTION OF THE DRAWINGS

An exemplary embodiment of the invention is represented in the attached schematic drawings, in which:

FIG. 2 shows a questionnaire.

DESCRIPTION OF THE PREFERRED EMBODIMENTS

Figure 1:
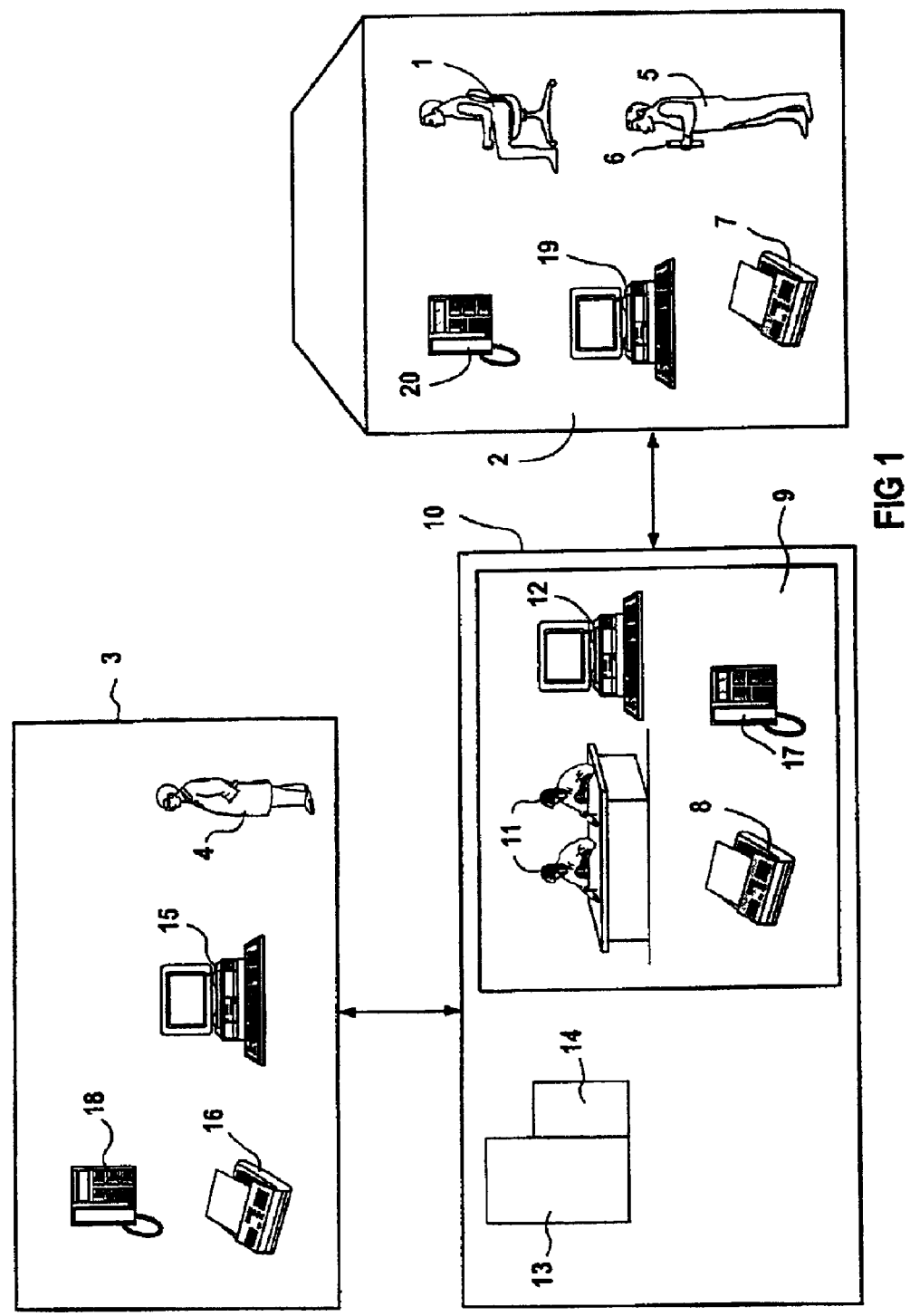
FIG. 1 shows a diagram of a medical system according to the invention.

Shown schematically in FIG. 1 is a patient 1 at his home 2, the patient having undergone an operation in a hospital 3 and been discharged to go home by his doctor 4 after the operation. During the operation, in the case of the present exemplary embodiment, a general anesthesia with intubation was carried out on the patient 1, exposing the patient 1 to an increased risk of developing an inflammation of the lungs as a typical postoperative complication. Therefore, in the case of the present exemplary embodiment, the patient 1 is visited once every day by a caregiver 5, who ascertains data on the patient 1 relevant for detecting pulmonary complications, such as for example an inflammation of the lungs as a typical postoperative complication.

In order that some of the relevant data are not inadvertently forgotten during the ascertainment of the relevant data, the caregiver 5 has a questionnaire 6, which is assigned to the patient 1, is shown by way of example in FIG. 2 and serves at the same time as a checklist for ascertaining the relevant data.

As shown in FIG. 2, the relevant data in the case of the present exemplary embodiment comprise information on the general condition of the patient 1 and information specifically suitable for detecting a pulmonary complication. In order to obtain the relevant data, the caregiver 5 asks the patient 1 about his physical capabilities, his bowel movement and his appetite or ascertains the occurrence of coughing or expectoration and notes the corresponding answers on the questionnaire 6. Subsequently, the caregiver 5 ascertains the temperature, the pulse, the blood pressure, the blood sugar level and the respiration rate of the patient 1 with measuring instruments which are generally known and not shown in FIG. 1, such as for example a fever thermometer, a blood-pressure measuring instrument, urine sticks, etc., and notes the corresponding values on the questionnaire 6.

Subsequently, the caregiver 5 faxes the questionnaire 6 by a fax machine 7 arranged at the home 2 of the patient 1 to a fax machine 8 which is arranged at a call center 9 of a service provider 10. One of the persons 11 working at the call center 9 enters the relevant data, transmitted by means of the faxed questionnaire, in a computer 12 which is arranged at the call center 9 and is connected to a data bank 13 in a way not represented in FIG. 1. The relevant data are stored in the data bank 13 with the identity of the patient 1 and the date on which the relevant data were ascertained.

In the case of the present exemplary embodiment, the data bank 13 is assigned an evaluation device 14, which checks the relevant data, in particular for completeness and plausibility. Furthermore, the evaluation device 14 compares the relevant data with comparison values, which in the case of the present exemplary embodiment are assigned to a person who has no postoperative complication and, in particular, no pulmonary complication. A person without postoperative complications has, for example, good to moderate physical capabilities and a good to moderate appetite. He has furthermore a normal temperature, that is to say no fever, and unremarkable bowel movement, normal blood pressure, etc.

The doctor 4 can, if he considers it necessary, also change the comparison values himself. If, in the case of the present exemplary embodiment, one of the values of the relevant data deviates from the corresponding comparison value, the evaluation device 14 classifies the relevant data as critical and the data bank 13 automatically sends an email to a computer 15 arranged at the hospital 3, in order to inform the doctor 4 about the critical relevant data. In particular in the event of a disrupted Internet connection, this message can be conveyed to the doctor 4 by one of the persons 11 by means of the fax machine 8 and a fax machine 16 arranged at the hospital 3 or by means of a telephone 17 arranged at the call center 9 and a telephone 18 arranged at the hospital 3.

In the case of the present exemplary embodiment, it is further provided that the data bank 13 can be contacted via the Internet. For example, when informed by the data bank 13 or by one of the persons 11, the doctor 4 can contact the data bank 13 by the computer 15 and ask for the relevant data on the patient 1. On the basis of this inquiry, the doctor 4 can possibly infer that the patient 1 has a pulmonary complication and, if necessary, initiate remedial measures for the patient 1.

If relevant data are incomplete or implausible, the data bank 13 informs the patient 1, automatically in the case of the present exemplary embodiment, by an e-mail, which is sent to a computer 19 arranged at the home 2 and connected to the Internet. Alternatively, one of the persons 11 may also notify the patient 1 by means of a telephone 20 arranged at the home 2.

If, on one day, the relevant data are inadvertently not transmitted to the data bank 13, the data bank 13 automatically informs the doctor 4 and the patient 1. In this way, a continuous postdischarge surveillance of the patient 1 is ensured.

Another possibility for transmitting the relevant data on the patient 1 to the data bank 13 is the use of the computer 19 connected to the Internet. In the case of the present exemplary embodiment, the patient 1 or the caregiver 5 uses the computer 19 to contact a WWW home page assigned to the patient 1 and maintained by the service provider 10. The WWW home page comprises the questionnaire 6 shown in FIG. 2. The patient 1 or the caregiver 5 subsequently ascertains the relevant data, specified on the questionnaire 6 and already described above, and enters them in the questionnaire 6 of the WWW home page. Once the relevant data have been entered in the questionnaire 6, they are transmitted to the data bank 13 and evaluated by the evaluation device 14.

A further possibility for transmitting the relevant data is that the patient 1 or the caregiver 5 transmits the relevant data by telephone to one of the persons 11 of the call center 9.

The relevant data of the present exemplary embodiment are to be understood as given only by way of example. The relevant data do not necessarily have to comprise a description of the general condition of the patient 1. The relevant data may also comprise other or further information, in particular concerning further typical postoperative complications, such as urinary tract infections, secondary bleeding, leg and pelvic venous thromboses, hypoglycemia and wound healing problems. The noting on a questionnaire 6 is also optional.

The patient 1 does not necessarily have to be kept under surveillance by a caregiver 5. He may also be kept under surveillance by a relative or can ascertain the relevant data himself and transmit them at least indirectly to the data bank 13.

The evaluation device 14 may also have an expert system. The expert system can, for example, interpret the relevant data on the basis of control systems or on the basis of probabilities. In this case, an individualization of the expert system to the patient 1 can be envisaged, i.e. the expert system gets to know the patient 1 it is keeping under surveillance better and better during the surveillance process; for this purpose, as a learning system, it continually makes forecasts on expected future relevant data, which it compares with the true relevant data. In this way, an individualized surveillance is achieved.

The data bank 13 may also be provided with means suitable for voice input and voice reproduction. Then the patient 1 or the caregiver 5 can contact the data bank 13 directly by telephone and transmit the relevant data by telephone to the data bank 13 on the basis of an interactive program procedure stored on the data bank 13.

Measuring instruments for ascertaining the relevant data which can be connected to the computer 19 may also be used. It is then possible to transmit the measurement results, that is relevant data, directly to the data bank 13, whereby possible incorrect reading of a measurement result can be avoided.

The service provider 10 does not necessarily have to have a call center 9. The data bank 13 also need not be operated by a service provider 10. It can, for example, also be arranged at the hospital 3.

Contacting the data bank 13 via the Internet is likewise optional. Although automatic alerting of the doctor 4 when there are critical relevant data is desirable, this feature is also optional. It may also be some other person, and other persons can also be alerted. The comparison values may also be set differently than described above. In particular, it is also conceivable to obtain the comparison values over time from the normalization of already recorded relevant data. For example, the average course of painkiller consumption after a specific operation of a number of patients who had no complications could be ascertained and stored in the data bank 13. The average course of painkiller consumption can then serve as a comparison value.

The alerting of the patient 1 or another person when the relevant data are not transmitted to the data bank 13 is likewise optional.

The patient 1 also does not necessarily have to be based at home 2, as long as he is under postdischarge surveillance.

The relevant data also do not have to to be ascertained and/or transmitted daily or periodically in general.

The surveillance relates not just exclusively to postoperative complications but generally also to complications which a patient can have after a stay in hospital.

What is claimed is:

1. A method for monitoring a patient after the patient has been postoperatively discharged from a medical facility, the method comprising the steps of:

at a location of the patient during the monitoring after the patient has been postoperatively discharged from the facility, providing the patient with a written questionnaire that gathers from the patient data suitable for detecting in the patient at least one of pneumonia, secondary bleeding, a wound healing problem, a pulmonary complication, a urinary tract infection, and a thrombosis;

conveying the patient data in the written questionnaire to a data bank over a telephone connection using one of a voice transmission and a facsimile transmission; and automatically evaluating the conveyed data with an evaluating device that is associated with the data bank.

2. The method of claim 1, further comprising the step of monitoring receipt of the patient data at the data bank and sending a signal to at least one of the patient and a caregiver when the patient data are not received.

3. The method of claim 1, further comprising the step of sending an alarm signal to at least one of the patient and a caregiver when the evaluating device indicates that the patient data are critical.

4. A method for monitoring a patient after the patient has been postoperatively discharged from a medical facility, the method comprising the steps of:
- providing on a world wide web site a questionnaire that is accessible with a computer at a location of the patient during the monitoring after the patient has been postoperatively discharged from the medical facility and that is connected to a communication network;
- entering patient data in the questionnaire with the computer, the patient data being suitable for detecting in the patient at least one of pneumonia, secondary bleeding, a wound healing problem, a pulmonary complication, a urinary tract infection, and a thrombosis;
- conveying the patient data in the questionnaire to a data bank over the communication network; and
- automatically evaluating the patient data with an evaluating device that is associated with the data bank.

5. The method of claim 4, further comprising the step of monitoring receipt of the patient data at the data bank and sending a signal to at least one of the patient and a caregiver when the patient data are not received.

6. The method of claim 4, further comprising the step of sending an alarm signal to at least one of the patient and a caregiver when the evaluating device indicates that the patient data are critical.

7. A system for monitoring a patient after the patient has been postoperatively discharged from a medical facility, the system comprising:
- a data bank at a location different from a location of the patient during the monitoring after the patient has been postoperatively discharged from the medical facility, said data bank being arranged and adapted to store patient data indicating in the patient at least one of pneumonia, secondary bleeding, a wound healing problem, a pulmonary complication, a urinary tract infection, and a thrombosis, the patient data being in a written questionnaire at the location of the patient during the monitoring;
- a telephone connection that connects said data bank to the location of the patient during the monitoring and that is arranged and adapted to convey the patient data in the written questionnaire to said data bank with one of a voice transmission and a facsimile transmission;
- an evaluation device that is operatively connected to said data bank and that is arranged and adapted to evaluate the patient data in said data bank; and
- an alarm that generated an alarm signal in response to an indication from said evaluation device that the patient data are critical.

8. The system of claim 7, wherein said data bank is further arranged and adapted to monitor receipt of the patient data at said data bank and to send a signal to at least one of the patient and a caregiver when the patient data are not received.

9. A system for monitoring a patient after the patient has been postoperatively discharged from a medical facility, the system comprising:
- a world wide web site with a questionnaire that is accessible with a computer at a location of the patient during the monitoring after the patient has been postoperatively discharged from the medical facility and that is connected to a communication network, the questionnaire gathering patient data indicating in the patient at least one of pneumonia, secondary bleeding, a wound healing problem, a pulmonary complication, a urinary tract infection, and a thrombosis;
- a data bank at a location different from the location of the patient during the monitoring, said data bank being connected to the communication network and arranged and adapted to receive and store the patient data in the questionnaire;
- an evaluation device that is operatively connected to said data bank and that is arranged and adapted to evaluate the patient data in said data bank; and
- an alarm that generates an alarm signal in response to an indication from said evaluation device that the patient data are critical.

10. The system of claim 9, wherein said data bank is further arranged and adapted to monitor receipt of the patient data at said data bank and to send a signal to at least one of the patient and a caregiver when the patient data are not received.

* * * * *